United States Patent
Sharif et al.

(10) Patent No.: US 11,130,933 B2
(45) Date of Patent: Sep. 28, 2021

(54) WET WIPES CONTAINING HYDROXY ACETOPHENONE AND COCAMIDOPROPYL PG DIMONIUM CHLORIDE PHOSPHATE

(71) Applicant: Rockline Industries, Sheboygan, WI (US)

(72) Inventors: Zahid I. Sharif, Bentonville, AR (US); Douglas B. Cole, Belgium, WI (US)

(73) Assignee: Rockline Industries, Inc., Sheboygan, WI (US)

( * ) Notice: Subject to any disclaimer, the term of this patent is extended or adjusted under 35 U.S.C. 154(b) by 45 days.

(21) Appl. No.: 15/410,968

(22) Filed: Jan. 20, 2017

(65) Prior Publication Data

US 2017/0204351 A1  Jul. 20, 2017

Related U.S. Application Data

(60) Provisional application No. 62/280,856, filed on Jan. 20, 2016.

(51) Int. Cl.
| | | |
|---|---|---|
| C11D 17/04 | (2006.01) | |
| C11D 3/20 | (2006.01) | |
| C11D 3/48 | (2006.01) | |
| C11D 3/36 | (2006.01) | |
| C11D 1/34 | (2006.01) | |
| C11D 3/30 | (2006.01) | |
| A61K 8/02 | (2006.01) | |
| A61K 8/55 | (2006.01) | |
| A61K 8/35 | (2006.01) | |
| A61Q 17/00 | (2006.01) | |
| A61Q 19/10 | (2006.01) | |
| A61Q 19/00 | (2006.01) | |

(52) U.S. Cl.
CPC .......... *C11D 17/049* (2013.01); *A61K 8/0208* (2013.01); *A61K 8/35* (2013.01); *A61K 8/553* (2013.01); *A61Q 17/005* (2013.01); *A61Q 19/00* (2013.01); *A61Q 19/10* (2013.01); *C11D 1/342* (2013.01); *C11D 3/2034* (2013.01); *C11D 3/2072* (2013.01); *C11D 3/30* (2013.01); *C11D 3/361* (2013.01); *C11D 3/48* (2013.01); *A61K 2800/524* (2013.01)

(58) Field of Classification Search
None
See application file for complete search history.

(56) References Cited

U.S. PATENT DOCUMENTS

| | | | |
|---|---|---|---|
| 4,540,505 | A | 9/1985 | Frazier |
| H269 | H | 5/1987 | Malik |
| 4,868,217 | A | 9/1989 | Araki et al. |
| 5,421,898 | A | 6/1995 | Cavanagh |
| 5,444,094 | A | 8/1995 | Malik et al. |
| 5,476,615 | A | 12/1995 | Hall et al. |
| 5,522,942 | A | 6/1996 | Graubart et al. |
| 5,529,713 | A | 6/1996 | Gauthier-Fournier |
| 5,814,591 | A | 9/1998 | Mills et al. |
| 5,908,854 | A | 6/1999 | McCue et al. |
| 6,004,916 | A | 12/1999 | , I |
| 6,013,615 | A | 1/2000 | Zhou et al. |
| 6,017,869 | A | 1/2000 | Lu et al. |
| 6,022,841 | A | 2/2000 | Lu et al. |
| 6,080,706 | A | 6/2000 | Blanvalet et al. |
| 6,140,289 | A | 10/2000 | McCandtish et al. |
| 6,159,916 | A | 12/2000 | Robbins et al. |
| 6,159,924 | A | 12/2000 | Weller et al. |
| 6,187,737 | B1 | 2/2001 | Gekeetal |
| 6,242,402 | B1 | 6/2001 | Robbins et al. |
| 6,245,728 | B1 | 6/2001 | Robbins |
| 6,284,723 | B1 | 9/2001 | Zhou et al. |
| 6,372,701 | B2 | 4/2002 | Aszman et al. |
| 6,399,555 | B2 | 6/2002 | Robbins et al. |
| 6,429,183 | B1 | 8/2002 | Leonard et al. |
| 6,444,214 | B1 | 9/2002 | Cole et al. |
| 6,673,761 | B2 | 1/2004 | Mitra et al. |
| 6,693,070 | B1 | 2/2004 | Cheung et al. |
| 6,716,805 | B1 | 4/2004 | Sherry et al. |
| 6,794,352 | B2 | 9/2004 | Svendsen |
| 6,814,974 | B2 | 11/2004 | Cole et al. |
| 6,825,158 | B2 | 11/2004 | Mitra et al. |
| 6,841,527 | B2 | 1/2005 | Mitra et al. |
| 6,844,308 | B1 | 1/2005 | Dastbaz et al. |
| 6,849,589 | B2 | 2/2005 | Liu |
| 6,915,776 | B2 | 7/2005 | Svendsen |

(Continued)

FOREIGN PATENT DOCUMENTS

WO  WO2014135650  *  9/2014

OTHER PUBLICATIONS

Kabara et al., "Preservative-Free and Self-Preserving Cosmetics and Drugs", CRC Press, 1997, pp. 145 and 147-148.*
L. Rajab et al., "Acetophenones with selective antimycobacterial activity", Letters in Applied Microbiology 2005, 40, 212-217.
Symrise, "Product Information, Symsave(R) H", http://chemical-centre.com/d/982327/d/symsameh.pdf, published Oct. 14, 2015.
AU Application No. 2017210203, Examination Report, 6 pages, dated Jun. 24, 2020.
Gangopadhyay, N. et al., "A Review of Extraction and Analysis of Bioactives in Oat and Barley and Scope for Use of Novel Food Processing Technologies", Molecules, 2015, vol. 20, pp. 10884-10909.

(Continued)

*Primary Examiner* — Robert A Wax
*Assistant Examiner* — Randeep Singh
(74) *Attorney, Agent, or Firm* — Boyle Fredrickson, S.C.

(57) ABSTRACT

A cleaning composition including a preservative formulation having hydroxy acetophenone and a phospholipid complex is disclosed. The cleaning composition can be loaded on a cleaning wipe and used for personal care. The hydroxyacetophenone provides a preservative booster to the preservative system for the cleaning composition containing a phospholipid complex, such as cocamidopropyl PG-dimonium chloride phosphate, which has some limited independent preservation activity, depending on the level in the final formulation.

19 Claims, No Drawings

(56) References Cited

U.S. PATENT DOCUMENTS

| | | |
|---|---|---|
| 6,936,580 B2 | 8/2005 | Sherry et al. |
| 6,951,834 B2 | 10/2005 | Mitra et al. |
| 7,101,612 B2 | 9/2006 | Lang et al. |
| 7,189,686 B2 | 3/2007 | Burt et al. |
| 7,345,015 B1 | 3/2008 | Kong et al. |
| 7,414,017 B2 | 8/2008 | Kong et al. |
| RE40,495 E | 9/2008 | Svendsen |
| 7,470,656 B2 | 12/2008 | Sherry et al. |
| 7,576,047 B2 | 8/2009 | Kilkenny et al. |
| 7,741,263 B2 | 6/2010 | Kilkenny et al. |
| 7,799,751 B2 | 9/2010 | Kilkenny et al. |
| 7,838,447 B2 | 11/2010 | Clark et al. |
| 7,915,184 B2 | 3/2011 | Ellis et al. |
| 8,193,104 B2 | 6/2012 | Parsons et al. |
| 8,455,551 B2 | 6/2013 | Heisig et al. |
| 8,486,427 B2 | 7/2013 | Colman et al. |
| 8,648,027 B2 | 2/2014 | Mitchell et al. |
| 9,006,165 B2 | 4/2015 | Mitchell et al. |
| 9,096,821 B1 | 8/2015 | Hope et al. |
| 9,234,165 B2 | 1/2016 | Hope et al. |
| 9,320,395 B2 | 4/2016 | Zwick et al. |
| 2001/0044393 A1 | 11/2001 | Peterson, Jr. et al. |
| 2002/0022660 A1 | 2/2002 | Jampani et al. |
| 2002/0031486 A1 | 3/2002 | Lunsmann et al. |
| 2002/0183233 A1 | 12/2002 | Mitra et al. |
| 2003/0022941 A1 | 1/2003 | Taylor et al. |
| 2003/0100465 A1 | 5/2003 | Kilkenny et al. |
| 2003/0109411 A1 | 6/2003 | Kilkenny et al. |
| 2004/0194800 A1 | 10/2004 | Chang et al. |
| 2005/0008680 A1* | 1/2005 | Deckner et al. |
| 2005/0245151 A1 | 11/2005 | Annis et al. |
| 2006/0166849 A1 | 7/2006 | Kilkenny et al. |
| 2012/0034287 A1 | 2/2012 | Napolitano et al. |
| 2015/0001066 A1 | 1/2015 | Joshi |
| 2015/0017215 A1 | 1/2015 | Wahal et al. |
| 2016/0021888 A1 | 1/2016 | Burke et al. |
| 2016/0075978 A1 | 3/2016 | Hope et al. |

OTHER PUBLICATIONS

Zhou, M. et al., "Oat lipids", Journal of American Oil Chemists' Society, 1999, vol. 76, pp. 159-169.

AU Application No. 2017210203, Examination Report No. 2, 6 pages, dated May 12, 2021.

* cited by examiner

WET WIPES CONTAINING HYDROXY ACETOPHENONE AND COCAMIDOPROPYL PG DIMONIUM CHLORIDE PHOSPHATE

CROSS-REFERENCE TO RELATED APPLICATIONS

The present application claims priority from U.S. Provisional Patent Application Ser. No. 62/280,856, filed on Jan. 20, 2016, the entirety of which is expressly incorporated by reference for all purposes.

FIELD OF THE INVENTION

The present invention relates to a cleaning composition comprising hydroxyacetophenone and a phospholipid complex.

BACKGROUND OF THE INVENTION

Increasing number of consumers are seeking cleaning products that not only are more natural or sustainable, but which also exhibit better overall safety of use. Consumers prefer products that can be readily used around children and pets in convenient forms such as pre-loaded disposable wipes or ready to use sprays, but these safer and more sustainable products still are expected to deliver performance on many attributes, such as cleaning and reduction of germs, at parity to traditional products.

In particular, wet wipes, or cleaning wipes, have gained wide public acceptance in the area of infant care products. Infant care wipes commonly include mild cleaning solutions, while facial wipes can include emulsions (i.e. water-in-oil or oil-in-water). Cleaning wipes can also include waxes and polish to clean furniture and/or other metal, plastic and/or wood surfaces. Wet wipes can further include soaps and/or detergents to clean an individual's hands, countertops, floors, appliances, and/or the like. An additional ingredient is ammonia for cleaning glass surfaces. Short chain alcohols and various, other biocides can also be included on cleaning wipes to disinfect or sanitize a variety of surfaces.

Traditional wet wipe preservation systems used in personal care applications continue to present challenges to effectively control microbial growth, which is inherent and part of the natural bioburden that occurs in raw materials and during manufacturing, storage and consumer use. Many preservative ingredients found in personal care wet wipe that have been used for many years are no longer regulatory compliant or fail to work effectively.

In view of the present state of the art of cleaning compositions for wet wipes, there is a need for an improved preservative composition for inclusion within a wet wipe cleaning formulation that can be used in a variety of applications related to personal care, surface cleaning, antibacterial, disinfects, sanitizers, and/or surfaces without the deficiencies presented above.

SUMMARY OF THE INVENTION

In light of the foregoing, in one exemplary embodiment the invention is directed to an effective self-preservation system or broad-spectrum antimicrobial enhancement activity composition for wet wipes. The self-preservation system or broad-spectrum antimicrobial enhancement activity composition is a formulation that comprises hydroxy acetophenone and a phospholipid. Examples of such phospholipids include alkyl PG-dimonium chloride phosphates with a fatty acid chain length between 8 and 20 carbons. Self-preservation is achieved by combining functional ingredients that collectively produce an environment that is unfavorable for the growth of microorganisms.

According to another exemplary embodiment of the invention, other components are optionally present in the cleaning composition including the preservative formulation, such as, for example, water, surfactants, emollients, solvents, skin conditioning agents, humectants, fragrances, botanical extracts, oils, silicones and the like, and combinations of the same. All components of the formulation are blended together to form a wet wipe composition, solution or emulsion that can be impregnated within or otherwise applied to a nonwoven, cloth or paper substrate, or combinations of the same to form a usable wet wipe that is sufficiently preserved for storage and consumer use.

According to one aspect of an exemplary embodiment of the invention, a method of cleaning a surface includes the steps of providing a cleaning composition having a preservative including hydroxy acetophenone and an organic phospholipid and applying the cleaning composition to surface.

According to still another aspect of an exemplary embodiment off the invention, a cleaning wipe includes a substrate and a cleaning composition loaded onto the substrate. the cleaning composition formed of preservative composition having a hydroxyacetophenone and an alkyl PG-dimonium chloride phosphate.

According to still a further aspect of an exemplary embodiment of the invention, a cleaning composition includes a preservative composition having a hydroxy acetophenone and an organic phospholipid for use as a preservative and/or anti-microbial component of the cleaning composition.

Without limitation then, in other exemplary embodiments this invention is also a wet wipe, or cleaning wipe, comprising a formulation comprising at least one layer of a nonwoven material, and a cleaning composition with a preservative component comprising hydroxy acetophenone and alkyl PG-dimonium chloride phosphates with a fatty acid chain length between 8 and 20 carbons. In one aspect, other components are optionally present in the cleaning composition, such as, for example, water, surfactants, emollients, solvents, skin conditioning, agents, humectants, fragrances, botanical extracts, oils, silicones and the like, and combinations of the same.

Other features, benefits and advantages of the present invention will be apparent from this summary and its descriptions of certain embodiments of such formulations and compositions, and will be readily apparent to those skilled in the art having knowledge of the synthetic techniques described therewith. Such features, benefits and advantages will be apparent from the above as taken into conjunction with the accompanying examples, data, and all reasonable inferences to be drawn therefrom.

DETAILED DESCRIPTION OF CERTAIN EMBODIMENTS

The invention relates to a formulation for a cleaning composition (or simply a "cleaning composition") comprising hydroxy acetophenone and a phospholipid complex. The cleaning composition of the invention can be used, for example, on personal care wet wipes such as baby wipes, facial wipes, moist toilet tissue, pet wipes, antibacterial wipes, hand-cleaning wipes and wipes for incontinence and feminine hygiene. As used herein, a "wipe" is a type of article suitable for cleansing or disinfecting or for applying a compound and/or removing materials and compounds from skin and surfaces, such as those disclosed in U.S. Pat. Nos. 7,101,612; 6,814,974; and 6,444,214, each of which is hereby expressly incorporated by reference in its entirety for all purposes, In particular, this term refers to an article for cleansing the body, including the removal of bodily waste.

Preferably, the phospholipid complex is an organic phospholipid. Nonlimiting examples of organic phospholipids include alkyl PG-dimonium chloride phosphates with a fatty acid chain length between 8 and 20 carbons, such as, for example, cocamidopropyl PG-dimonium chloride phosphate. Other non-limiting examples of suitable alkyl PG-dimonium chloride phosphates include sodium coco PG-dimonium chloride phosphate, stearamidopropyl PG-dimonium chloride phosphate, myristalamidopropyl PG-dimonium chloride phosphate, sodium borageamidopropyl PG-dimonium chloride phosphate, linoleamidopropyl PG-dimonium chloride phosphate, linoleamidopropyl PG-dimonium chloride phosphate dimethicone, and the like.

Referring to cocamidopropyl PG-dimonium chloride phosphate, specifically, the complex belongs to a family of products that are multifunctional, natural triglyceride phospholipids and are similar to phospholipids that occur naturally in the body. Cocamidopropyl PG-dimonium chloride phosphate is a coconut oil derived phospholipid composed predominantly of diester and triester phosphatides with multiple-chain groups. It displays a broad range of functional attributes including gentle cleansing and foaming properties, anti-irritation effects when combined with anionic or nonionic surfactants, unusually high substantivity, long-lasting skin conditioning, and broad spectrum anti-microbial activity. Cocamidopropyl PG-dimonium chloride phosphates generally have the following formula:

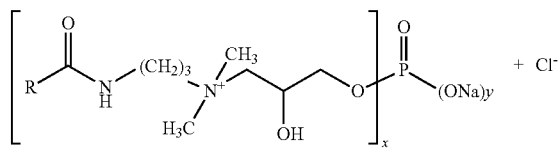

wherein the "R" group originates from coconut oil (i.e. $C_5$-$C_{20}$ alkyl) and "x"+"y" equals the integer 3.

As referred to herein, "hydroxy acteophenone" can be any of the isomers of hydroxyl acteophenone, but in one exemplary embodiment is p-hydroxy acetophenone, compound having the following structure:

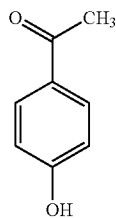

It is to be understood that the formulation for the cleaning composition can optionally include various other components or adjuncts. The hydroxy acetophenone, alkyl PG-dimonium chloride phosphates and various other components are blended together to form a wet wipe solution or emulsion that can be applied to a substrate to form a usable wet wipe that is sufficiently preserved for storage and consumer use.

The amount of hydroxy acetophenone in the final wet wipe solution is from 0.1% to 1.0% by weight, preferably 0.25% to 0.75% by weight. The amount of phospholipid complex (as part of the active ingredient) in the final wet wipe solution is 0.1% to 2.0% by weight, preferably 0.2% to 1.5% by weight. Hydroxyacetophenone and phospholipid complex is used in combination at above mentioned ratios to provide a robust, self-preserved anti-microbial and preservative formulation or system for use in cleaning composition such as utilized with various substrates to form wet wipes.

As stated above, the cleaning composition may optionally include and/or be used in combination with one or more additional components or adjuncts. The adjuncts include, but are not limited to, water, surfactants, emollients, fragrances and/or perfumes, botanical extracts, oils and/or lotions, silicones, waxes, dyes and/or colorants, solubilizing materials, stabilizers, thickeners, defoamers, hydrotropes, chelating agents, buffers, builders, enzymes, solvents, bleaching agents, cloud point modifiers, preservatives and/or combinations of the same. Any suitable solvent can be utilized with the preservative formulation and cleaning composition including the preservative formulation of the invention, but in certain exemplary embodiments the solvent is selected from $C_3$-$C_{10}$ glycols/diols, or from $C_5$-C8 glycols/diols.

In one exemplary embodiment of the present invention, the cleaning composition can be loaded onto an absorbent substrate. The absorbent substrate is preferably water-insoluble. By "water insoluble" is meant that the substrate does not dissolve but may readily break apart upon immersion in water. This cleaning composition can be used on flushable wipes in which the nonwoven substrate readily breaks apart after flushing. The water insoluble substrate is the implement or vehicle for delivering the cleaning composition of the present invention to the skin to be cleansed and moisturized. As used herein, the terms "substrate" or "wipe" are intended to include any material on which a cleaning composition may be loaded. In functional applications, a substrate is used to clean an article or a surface, as by wiping. Substrates comprise woven or non-woven materials, typically made from a plurality of fibers. The substrate can be used by itself (typically by hand) or attached to a cleaning implement, such as a floor mop, handle, or a handheld cleaning tool, such as a toilet cleaning device. A wide variety of materials can be used as the substrate. Nonlimiting examples of suitable water insoluble substrates include nonwoven substrates, woven substrates, sponges, cloths, meshes, paper towels, napkins, cleaning pads, and the like.

Preferred embodiments employ nonwoven substrates since they are economical and readily available in a variety of materials. By nonwoven is meant that the layer is comprised of fibers which are not woven into a fabric but rather are formed into a membrane, sheet, substrate, mat, absorbent core or pad layer or combinations thereof. Nonwoven substrates may be comprised of a variety of materials both natural and synthetic. By natural is meant that the materials are derived from plants, animals, insects or byproducts of plants, animals, and insects. By synthetic is meant that the materials are obtained primarily from various man-made materials or from natural materials which have been further altered. The conventional base starting material is usually a fibrous web comprising any of the common synthetic or natural textile-length fibers, or mixtures thereof. Non-limiting examples of natural materials useful in the present invention are silk fibers, keratin fibers and cellulosic fibers. Non-limiting examples of keratin fibers include those selected from the group consisting of wool fibers, camel hair fibers, and the like. Non-limiting examples of cellulosic fibers include those selected from the group consisting of wood pulp fibers, cotton fibers, hemp fibers, jute fibers, flax fibers, and mixtures thereof. Non-limiting examples of synthetic materials useful in the present invention include those selected from the group consisting of acetate fibers, acrylic fibers, cellulose ester fibers, modacrylic fibers, polyamide fibers, polyester fibers, polyolefin fibers, polyvinyl alcohol fibers, rayon fibers, polyurethane foam, and mixtures thereof. Examples of some of these synthetic materials include acrylics such as acrilan, creslan, and the acrylonitrile-based fiber, orlon; cellulose ester fibers such as cellulose acetate, arnel, and acele; polyamides such as nylons; polyesters such as fortrel, kodel, and the polyethylene terephthalate fiber, dacron; polyolefins such as polypropylene, polyethylene; polyvinyl acetate fibers; polyurethane foams and mixtures thereof.

Without being bound to any theory, the invention has shown that the hydroxyacetophenone provides a preservative booster to the preservative system containing a phospholipid complex (such as cocamidopropyl PG-dimonium chloride phosphate) which may have some limited preservation activity independently, depending on the level in the final formulation.

EXAMPLE 1

The following are the components and amounts of the same that represent a specific working example of the composition provided herein.
1) cocamidopropyl PG-dimonium chloride phosphate: 1.0%; 2) hydroxyacetophenone: 0.50%; 3) glycerin: 0.50%; 4) phenoxy ethanol 0.30%; 5) propanediol: 0.75%; 6) caprylyl glycol: 0.15%; 7) fragrance: 0.20%; and 8) citric acid 0.05%.

EXAMPLE 2

Table 1 represents a specific example of a composition according to the invention that can be loaded onto a cleaning wipe.

| Ingredient | % use level | % active/purity | % in final product |
|---|---|---|---|
| Water | 95.95 | 100 | 96.485 |
| Cocamidopropyl PG-Dimonium Chloride Phosphate | 1.00 | 46.5 | 0.465 |
| Glycerin | 0.50 | 100 | 0.50 |
| Phenoxvethanol | 0.50 | 100 | 0.50 |
| Propanediol | 0.75 | 100 | 0.75 |
| 1,2-Hexanediol | 0.50 | 100 | 0.50 |
| Hydroxvacetophenone | 0.50 | 100 | 0.50 |
| Fragrance | 0.20 | 100 | 0.20 |
| Citric Acid | 0.10 | 100 | 0.10 |

It is noted that the range of cleaning solution impregnated into the substrate includes from between 100% to 500% of the dry weight of the substrate.

The disclosures of all articles and references, including patents, are incorporated herein by reference. The invention and the manner and process of making and using it are now described in such full, clear, concise and exact terms as to enable any person skilled in the art to which it pertains, to make and use the same. All references cited in this specification are incorporated herein by reference. It is to be understood that the foregoing describes preferred embodiments of the present invention and that modifications may be made therein without departing from the spirit or scope of the present invention.

What is claimed is:

1. A preservative formulation for a wet wipe cleaning composition, the preservative formulation comprising:
    a first preservative compound formed of a hydroxy acetophenone; and
    a second preservative compound formed of an organic phospholipid, wherein the organic phospholipid is an alkyl PG-dimonium chloride phosphate.

2. A preservative formulation according to claim 1 wherein the alkyl PG-dimonium chloride phosphate has a fatty acid chain length between 8 and 20 carbons.

3. A preservative formulation according to claim 2 wherein the alkyl PG-dimonium chloride phosphate is cocamidopropyl PG-dimonium chloride phosphate.

4. A preservative formulation according to claim 2 wherein the alkyl PG-dimonium chloride phosphate is selected from the group consisting of cocamidopropyl PG-dimonium chloride phosphate, sodium coco PG-dimonium chloride phosphate, stearamidopropyl PG-dimonium chloride phosphate, myristalamidopropyl PG-dimonium chloride phosphate, sodium borageamidopropyl PG-dimonium chloride phosphate, linoleamidopropyl PG-dimonium chloride phosphate, and linoleamidopropyl PG-dimonium chloride phosphate dimethicone.

5. A preservative formulation according to claim 1 wherein the alkyl PG-dimonium chloride phosphate has the following formula:

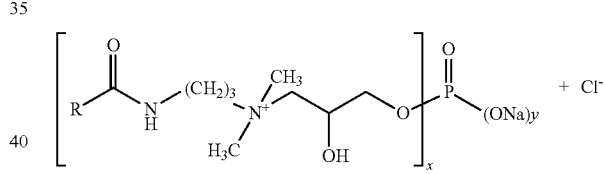

wherein the "R" group is a $C_8$-$C_{20}$ alkyl group and "x"+"y" equals the integer 3.

6. A preservative formulation according to claim 1 further comprising one or more adjuncts selected from a group consisting of water, surfactants, emollients, fragrances and/or perfumes, extracts, oils and/or lotions, silicones, waxes, dyes and/or colorants, solubilizing materials, stabilizers, thickeners, defoamers, hydrotropes, buffers, builders, enzymes, bleaching agents, cloud point modifiers and preservatives.

7. A preservative formulation according to claim 1 wherein the hydroxyl acetophenone has the following formula:

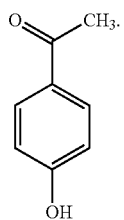

8. A preservative formulation according to claim 1 wherein the hydroxy acetophenone is present in the cleaning composition in an amount of from 0.1% to 1.0 by weight.

9. A preservative formulation according to claim 8 wherein the hydroxy acetophenone is present in the cleaning composition in an amount of from 0.25% to 0.75% by weight.

10. A preservative formulation according to claim 1 wherein the organic phospholipid is present in the cleaning composition in an amount of from 0.1% to 2.0% by weight.

11. A preservative formulation according to claim 10 wherein the organic phospholipid is present in the cleaning composition in an amount of from 0.2% to 1.5% by weight.

12. A cleaning wipe comprising a substrate and a cleaning composition loaded onto the substrate, the cleaning composition comprising a preservative formulation comprising a hydroxy acetophenone and an alkyl PG-dimonium chloride phosphate.

13. A cleaning wipe according to claim 12 wherein the alkyl PG-dimonium chloride phosphate has a fatty acid chain length between 8 and 20 carbons.

14. A cleaning wipe according to claim 12 wherein the alkyl PG-dimonium chloride phosphate is cocamidopropyl PG-dimonium chloride phosphate.

15. A cleaning wipe according to claim 12 wherein the substrate is a nonwoven substrate.

16. A cleaning wipe according to claim 12 further comprising one or more adjuncts selected from a group consisting of water, surfactants, emollients, fragrances and/or perfumes, extracts, oils and/or lotions, silicones, waxes, dyes and/or colorants, solubilizing materials, stabilizers, thickeners, defoamers, hydrotropes, buffers, builders, enzymes, bleaching agents, cloud point modifiers and preservatives.

17. A cleaning wipe according to claim 12 impregnated into a substrate, the substrate being from 100% to 500% of dry weight relative to the cleaning solution.

18. A preservative formulation for a wet wipe cleaning composition, the preservative formulation consisting of:
a first preservative compound formed of a hydroxy acetophenone; and
a second preservative compound formed of an organic phospholipid, wherein the organic phospholipid is an alkyl PG-dimonium chloride phosphate.

19. A method of enhancing bactericidal and fungicidal effects of a preservative formulation including an alkyl PG-dimonium chloride phosphate comprising:
adding a hydroxyacetophenone to the preservative formulation.

* * * * *